(12) United States Patent
Casadio

(10) Patent No.: US 10,408,769 B2
(45) Date of Patent: Sep. 10, 2019

(54) APPARATUS FOR OPTICAL INSPECTION OF OBJECTS

(71) Applicant: SACMI COOPERATIVA MECCANICI IMOLA SOCIETA' COOPERATIVA, Imola (Bologna) (IT)

(72) Inventor: Marco Casadio, Imola (IT)

(73) Assignee: SACMI COOPERATIVA MECCANICI IMOLA SOCIETA'COOPERATIVA, Imola (Bologna) (IT)

( * ) Notice: Subject to any disclaimer, the term of this patent is extended or adjusted under 35 U.S.C. 154(b) by 0 days.

(21) Appl. No.: 15/772,934

(22) PCT Filed: Dec. 12, 2016

(86) PCT No.: PCT/IB2016/057532
§ 371 (c)(1),
(2) Date: May 2, 2018

(87) PCT Pub. No.: WO2017/109635
PCT Pub. Date: Jun. 29, 2017

(65) Prior Publication Data
US 2018/0321163 A1    Nov. 8, 2018

(30) Foreign Application Priority Data
Dec. 22, 2015    (IT) .......................... 102015000086406

(51) Int. Cl.
*G01N 21/88* (2006.01)
*G01N 21/90* (2006.01)

(52) U.S. Cl.
CPC ....... *G01N 21/909* (2013.01); *G01N 21/8806* (2013.01); *G01N 21/9036* (2013.01); *G01N 2201/0633* (2013.01)

(58) Field of Classification Search
CPC .............. G01N 21/88; G01N 21/8803; G01N 21/8806; G01N 21/90; G01N 21/9036;
(Continued)

(56) References Cited

U.S. PATENT DOCUMENTS 3,187,174 A * 6/1965 Langer ...................... F21S 8/02
362/150
5,638,461 A * 6/1997 Fridge ..................... G01N 21/88
382/141
(Continued)

FOREIGN PATENT DOCUMENTS

EP    0961113 A1    12/1999
EP    1477794 A1    11/2004
(Continued)

OTHER PUBLICATIONS

Patent Cooperation Treaty (PCT) International Search Report and Written Opinion issued in PCT International Application No. PCT/IB2016/0575362, having an PCT International Filing Date of Dec. 12, 2016, dated Feb. 22, 2017 (15 pgs).

*Primary Examiner* — Gordon J Stock, Jr.
(74) *Attorney, Agent, or Firm* — Kraguljac Law Group, LLC

(57) ABSTRACT

An apparatus for optical inspection of objects, in particular cans. The apparatus includes an inspection station, a lighting system, and a camera directed towards the inspection system to capture an image of the lateral surface of the object to be inspected. A Fresnel lens is associated with the lighting system to direct a beam of light rays collimated towards the object to be inspected, located in the inspection station. A further Fresnel lens is positioned to face the object to be inspected, located in the inspection station and directed in such a way as to make the collimated light rays converge on the object.

20 Claims, 5 Drawing Sheets

(58) Field of Classification Search
CPC ........... G01N 21/9045; G01N 21/9054; G01N 21/909; G01N 21/95; G01N 21/9501; G01N 21/9515; G01N 21/952; G01N 2021/8816; G01N 2201/063; G01N 2201/0633
See application file for complete search history.

(56) References Cited

U.S. PATENT DOCUMENTS

| | | | |
|---|---|---|---|
| 6,364,511 B1 * | 4/2002 | Cohen | F21S 8/02 362/148 |
| 7,602,959 B2 * | 10/2009 | Song | G01N 21/8806 382/141 |
| 7,911,602 B2 | 3/2011 | Schlieper | |
| D753,328 S * | 4/2016 | Mathews | D26/63 |
| 2003/0184740 A1 | 10/2003 | Paradis | |
| 2005/0018897 A1 * | 1/2005 | Choi | G01N 21/8806 382/141 |
| 2006/0126060 A1 | 6/2006 | Colle et al. | |
| 2006/0209299 A1 * | 9/2006 | Vertoprakhov | G01N 21/8806 356/237.5 |
| 2010/0302539 A1 * | 12/2010 | Myrick | G01J 3/02 356/326 |
| 2011/0050884 A1 | 3/2011 | Niedermeier et al. | |
| 2012/0085895 A1 * | 4/2012 | Martin | G02B 27/0018 250/229 |
| 2013/0301904 A1 * | 11/2013 | Lee | G01N 21/8806 382/145 |

FOREIGN PATENT DOCUMENTS

| | | |
|---|---|---|
| EP | 1985997 A1 | 10/2008 |
| JP | 2002267611 A | 9/2002 |
| JP | 2002286435 A | 10/2002 |

* cited by examiner

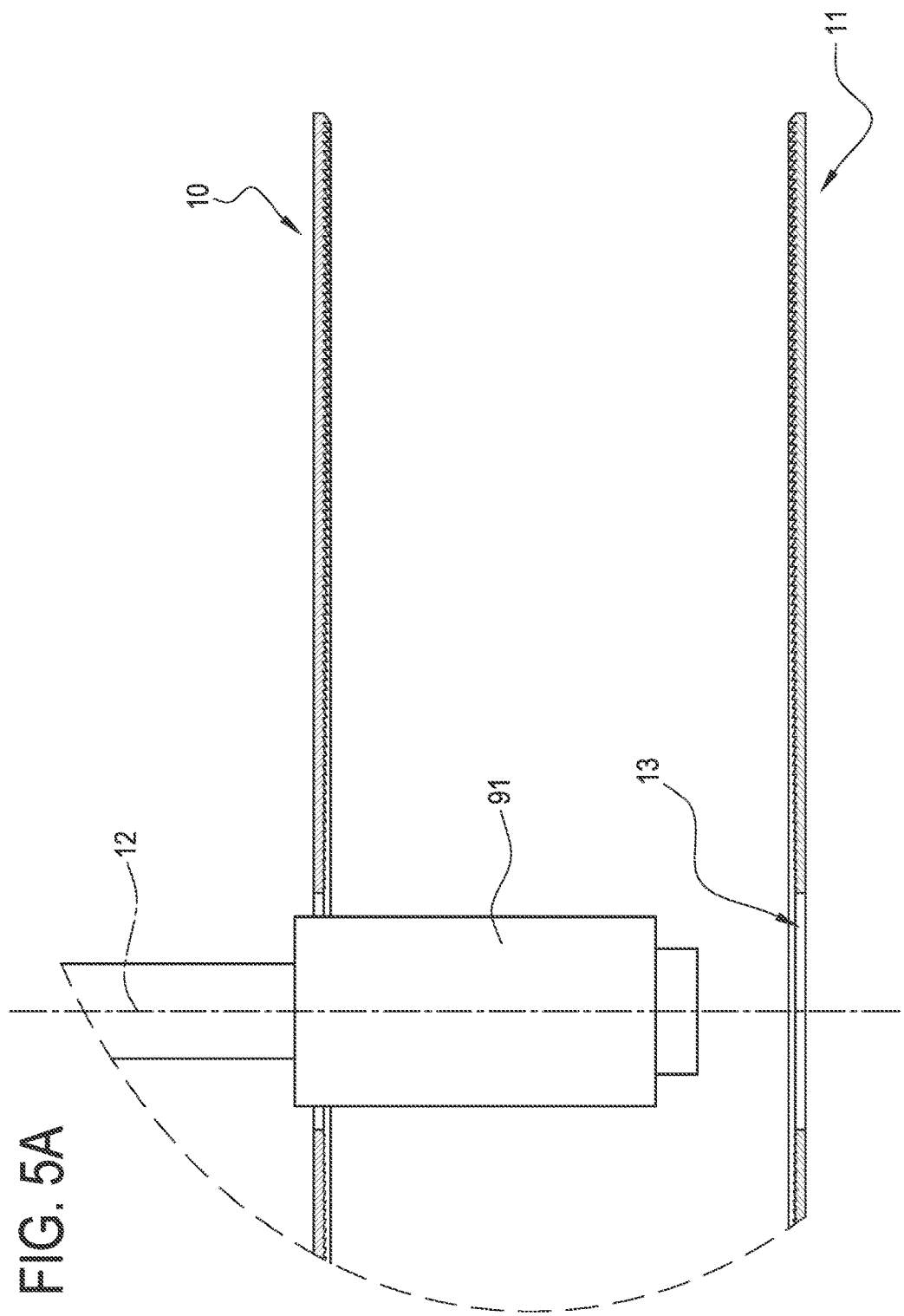

APPARATUS FOR OPTICAL INSPECTION OF OBJECTS

TECHNICAL FIELD

This invention relates to an apparatus for the optical inspection of objects. The invention can be advantageously applied to industrial processes for the optical inspection of the outside surface of metallic or metallescent objects, such as cans or the like, which this specification expressly refers to but without thereby losing in generality.

BACKGROUND ART

Procedures for the quality assurance of cans normally include optical inspection of the surface of the cans, not only to detect scratches or dents but also to detect possible defects of the decorative enamel coating previously applied to the surface of the cans by one or more rollers and subsequently fixed in an oven.

Optical inspection is usually conducted along the conveying section of a conveyor belt which transports the cans one after the other in a row. A lighting system is directed towards the conveying section so as to illuminate each can as it moves in the field of vision of a camera. Lastly, the image captured by the camera is compared with a reference image to determine whether the can inspected is to be accepted or rejected.

Examples of optical inspection apparatus are provided by patent documents EP1477794A1, EP0961113A1, EP1985997A1, US2011/050884A1, JP2002/267611A, U.S. Pat. No. 7,911,602B2, US2003/184740A1.

One drawback of prior art inspection systems is that the image of the can captured by the camera is undesirably affected by reflected light from the adjacent cans upstream and downstream of the can being inspected.

This drawback is due largely to the fact that the undecorated parts of the cans tend to reflect the incident light like a mirror.

In one possible solution to this drawback, the cans are spaced apart by a length such as to reduce or eliminate the effect of reflected light. This solution, however, means slowing down the optical inspection process, which in turn depends on the maximum speed at which the conveyor belt can run.

DISCLOSURE OF THE INVENTION

The aim of this invention is to provide an apparatus for optical inspection of objects to overcome the above mentioned drawbacks of the prior art.

This aim is fully achieved by the apparatus for optical inspection of objects according to the invention as characterized in the appended claims.

More specifically, the optical inspection apparatus according to this description is an apparatus for optically inspecting the lateral surface of objects transported in succession on a conveyor line.

Each of the objects is transported (for example on a conveyor) with a resting surface rested on a supporting surface (defined, for example, by the conveyor) and with a lateral surface made accessible for optical inspection.

The apparatus according to this description defines an inspection station in which an object to be inspected is placed, oriented along a longitudinal axis. Preferably, the longitudinal axis is vertical (perpendicular to the supporting surface which the object rests on).

The apparatus comprises a lighting system to illuminate the object to be inspected (located in the inspection station). The lighting system is located above the inspection station to illuminate the object from above.

The apparatus comprises at least one camera directed towards the inspection station to capture an image of the object to be inspected. Preferably, the apparatus comprises a plurality of these cameras.

The camera (or cameras) is directed towards the inspection station to capture an image of the lateral surface of the object to be inspected. For example, the apparatus comprises one or more cameras located laterally of the conveyor, that is, laterally of the object to be inspected in the inspection station.

In an example embodiment, the apparatus also comprises collimating means (that is, a collimating unit or a collimating element). The collimating means are configured to receive light rays from the lighting system. The collimating means are associated (or act in conjunction) with the lighting system to receive the light rays and are configured to direct a beam of collimated light rays towards the object to be inspected, located in the inspection station.

In an example embodiment, the apparatus comprises a converging lens. The converging lens is configured to receive the collimated light rays from the collimating means.

In an example embodiment, the converging lens is positioned to face the object to be inspected, located in the inspection station.

The converging lens is directed in such a way as to make the collimated light rays from the collimating means converge on the object.

Thus, the diverging light rays from the lighting system are first made parallel by the collimating means and then made to converge towards the inspection station in such a way as to obtain selective illumination of the object to be inspected.

In other words, only the object to be inspected is illuminated while the objects adjacent to it (in the context of the objects transported in succession) remain unlit.

The converging lens is interposed between the lighting system and the inspection station (that is, the object to be inspected).

The collimating means are interposed between the lighting system and the converging lens.

Preferably, the collimating means and the converging lens are aligned along a (vertical) longitudinal axis which coincides with the longitudinal axis of the object to be inspected situated in the inspection station.

Preferably, the converging lens is a (first) Fresnel lens. The size and weight of the inspection apparatus can thus be limited.

Preferably, the collimating means are defined by a (second) Fresnel lens. The size and weight of the inspection apparatus can thus be further limited.

Preferably, the first and second Fresnel lenses lie in respective parallel planes and their respective central axes of symmetry coincide with each other.

That way, the inspection apparatus is advantageously compact and the combined operation of the Fresnel lenses is optimized.

In an example embodiment, the apparatus comprises an upper camera configured to inspect the object in the inspection station from above.

For example, if the object to be inspected is a container which is open at the top, the upper camera makes it possible to see (and thus inspect) an inside surface of the object. Such an inspection constitutes a further inspection, additional to the aforementioned inspection of the lateral (outside) surface of the object.

In one embodiment, the upper camera is interposed between the first and the second Fresnel lens coaxially with the aforementioned central axis. That way, the camera is positioned in the region where the rays are collimated and does not therefore create an unwanted shadow on the inspection station.

In one embodiment, the first Fresnel lens has a through hole which is coaxial with the central axis and which delimits the field of vision of the camera. That way, the field of vision of the camera is not disturbed by the first Fresnel lens.

In one embodiment, the lighting system comprises at least one ring of LED lights extending around a respective axis of symmetry coaxial with the aforementioned central axis.

This configuration optimizes the illumination around the field of vision of the camera. More specifically, the illumination of the object to be inspected is uniform and well balanced between centre and periphery.

In an example embodiment, there is a cylindrical tubular element interposed between the ring of LED lights and the second Fresnel lens to convey the light rays towards the second Fresnel lens. Preferably, the tubular element is internally dark, for example black.

The function of the cylindrical tubular element is to confine the light rays to the inspection station only and further contributes to the selective illumination of the object to be inspected.

In one embodiment, the collimating means are configured to receive the light rays generated by the illumination system.

In one embodiment, the illumination system includes a source of light rays (in a non-limiting example, a ring of LED lights) positioned above the collimator means.

In one embodiment, the collimating means are distinct from the illumination system and placed at a predetermined distance from it.

In one embodiment, the source of light rays has a significantly smaller diameter than that of the converging lens; for example, the diameters are in a ratio of 1:3 or lower, or 1:5 or less, or 1:10 or less; in one embodiment, the source of light rays is substantially (or behaves substantially as) a point source.

BRIEF DESCRIPTION OF DRAWINGS

This and other features of the invention will become more apparent from the following detailed description of a preferred, non-limiting example embodiment of it, with reference to the accompanying drawings, in which:

FIG. 5A shows an enlargement of the detail A from FIG. 5.

DETAILED DESCRIPTION OF PREFERRED EMBODIMENTS OF THE INVENTION

Figure 1:
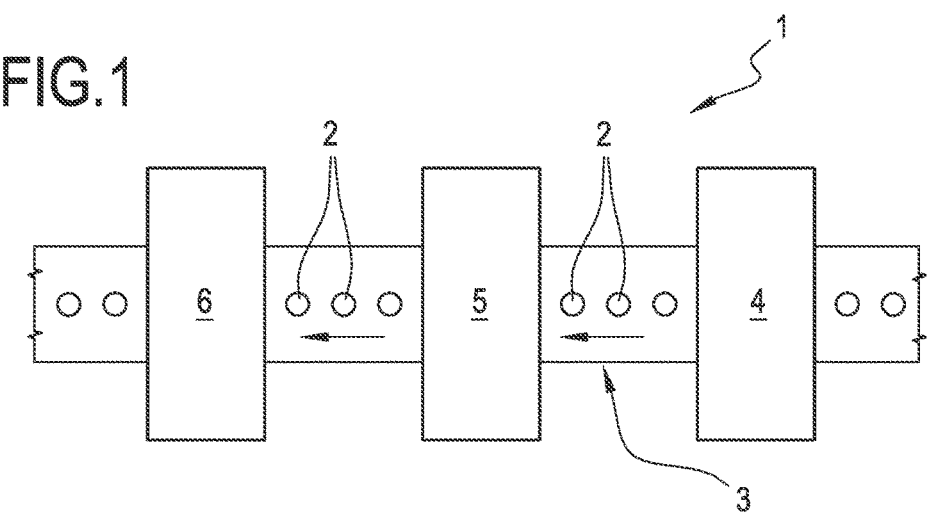
FIG. 1 schematically illustrates a line for the production of objects—in particular, cans—in which there is an inspection apparatus made according to this invention.

With reference to the drawings, the numeral 1 denotes in its entirety a line for the production of objects 2, in particular cans or similar objects.

The line 1 comprises a conveyor, defining a conveyor line 3 for the objects 2. The line 1 also comprises an enamelling unit 4, located along the conveyor line 3, for enamelling the outside surface of the objects 2. In one example embodiment, the line 1 comprises an oven 5 for drying the enamel applied to the objects 2 and located along the conveyor line 3, downstream of the enamelling unit 4. The line 1 also comprises an optical inspection apparatus 6 located along the conveyor line 3, downstream of the oven 5.

Figure 2:
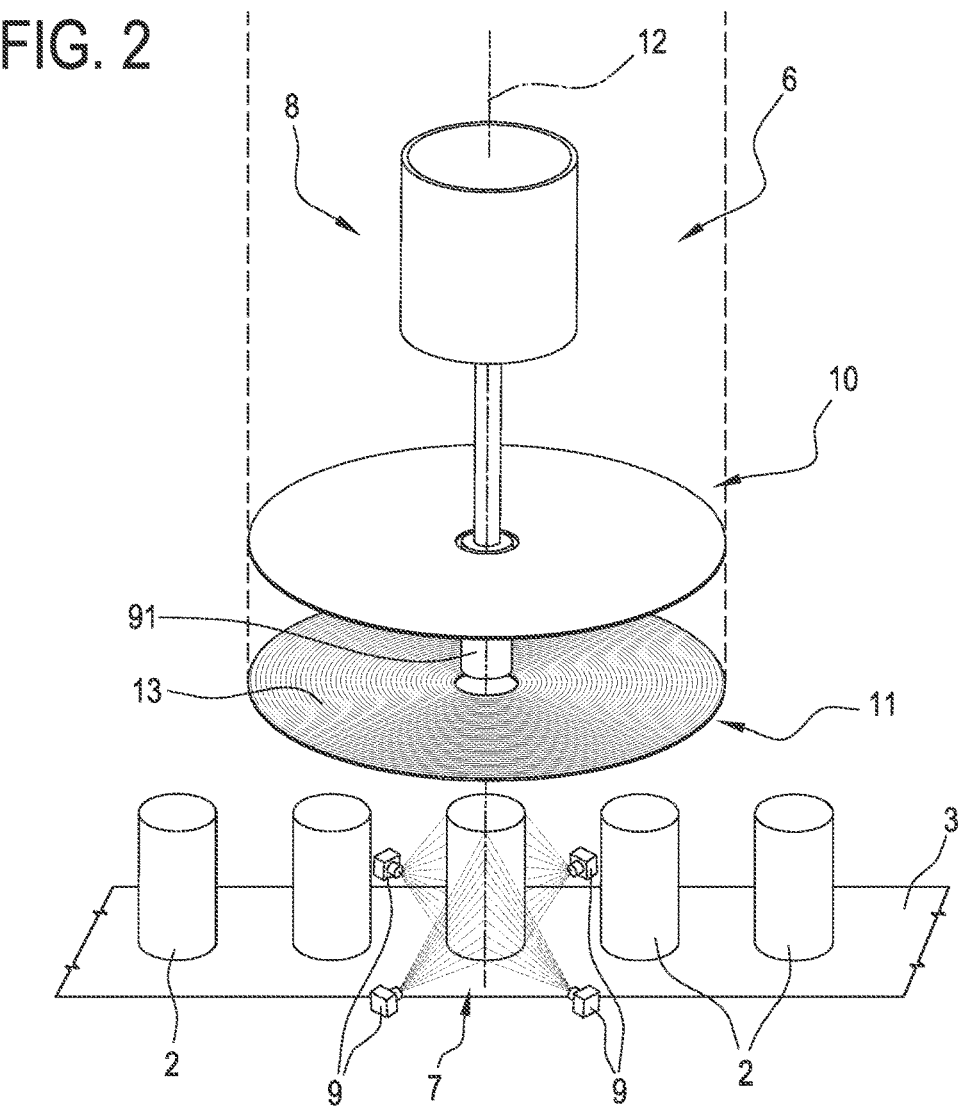
FIG. 2 illustrates an inspection apparatus according to this description.
Figure 3:
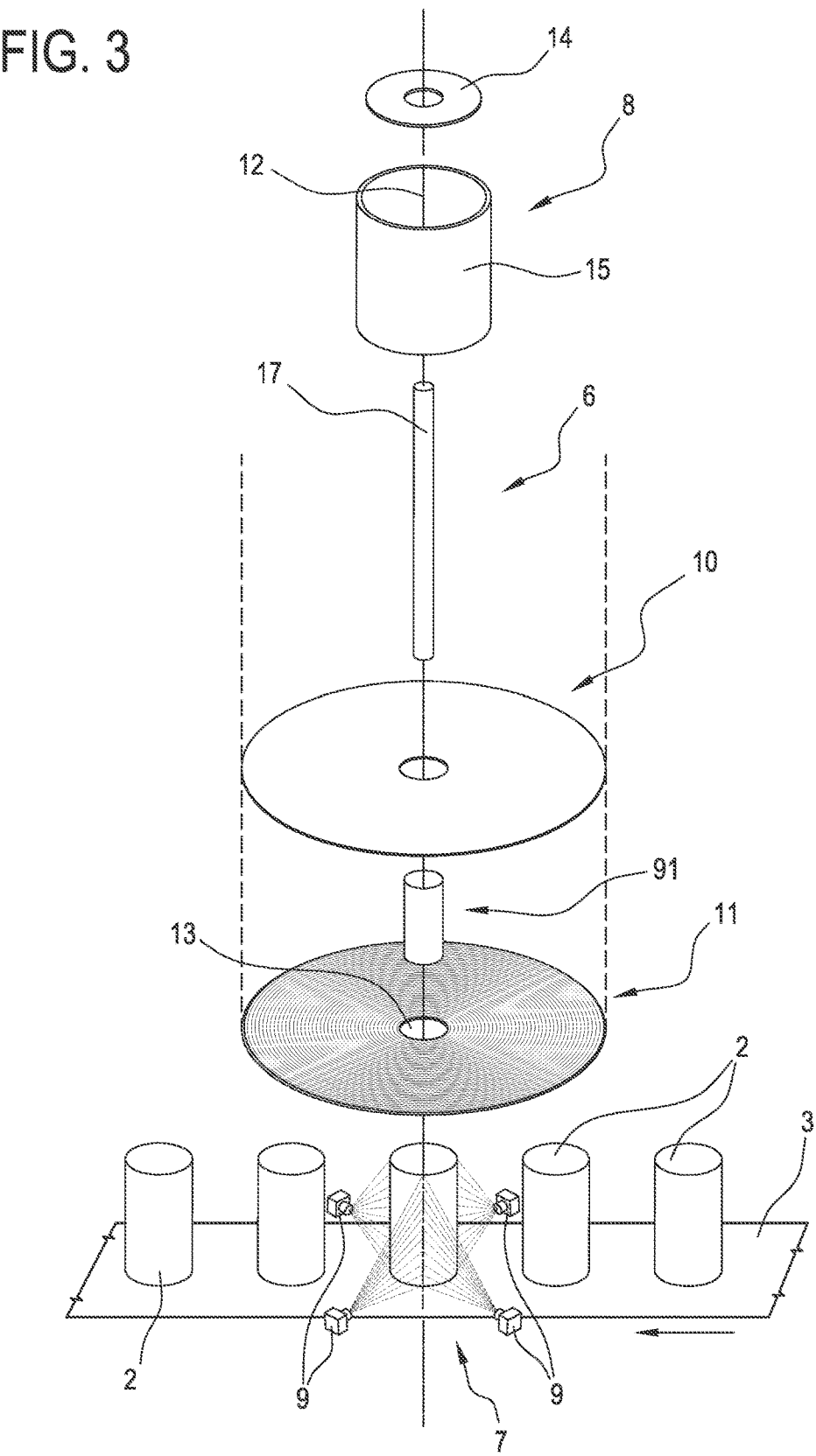
FIG. 3 is an exploded view of the apparatus of FIG. 2.
Figure 4:
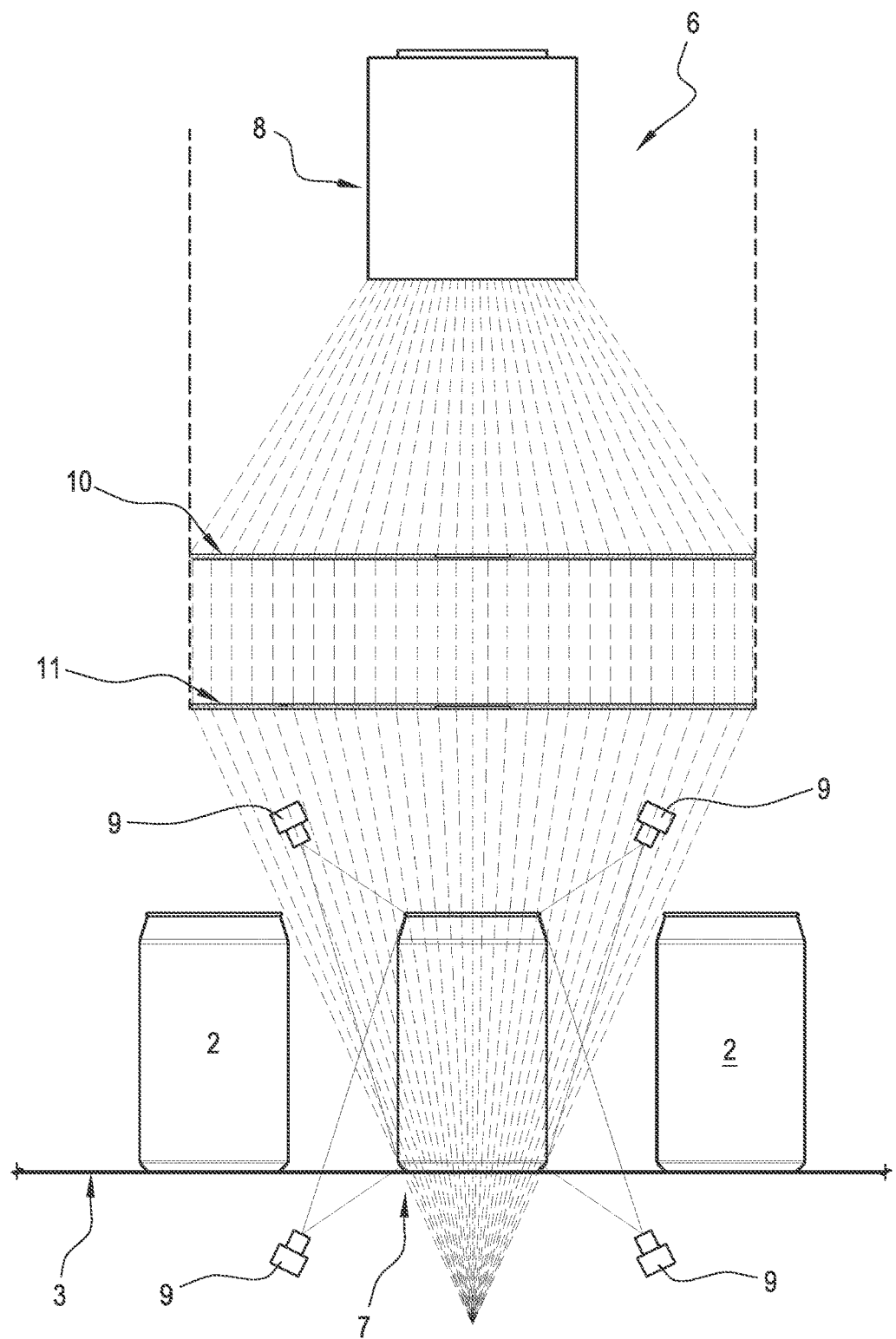
FIG. 4 is a schematic side view of an apparatus according to this description, simplified compared to that of FIG. 2.
Figure 5:
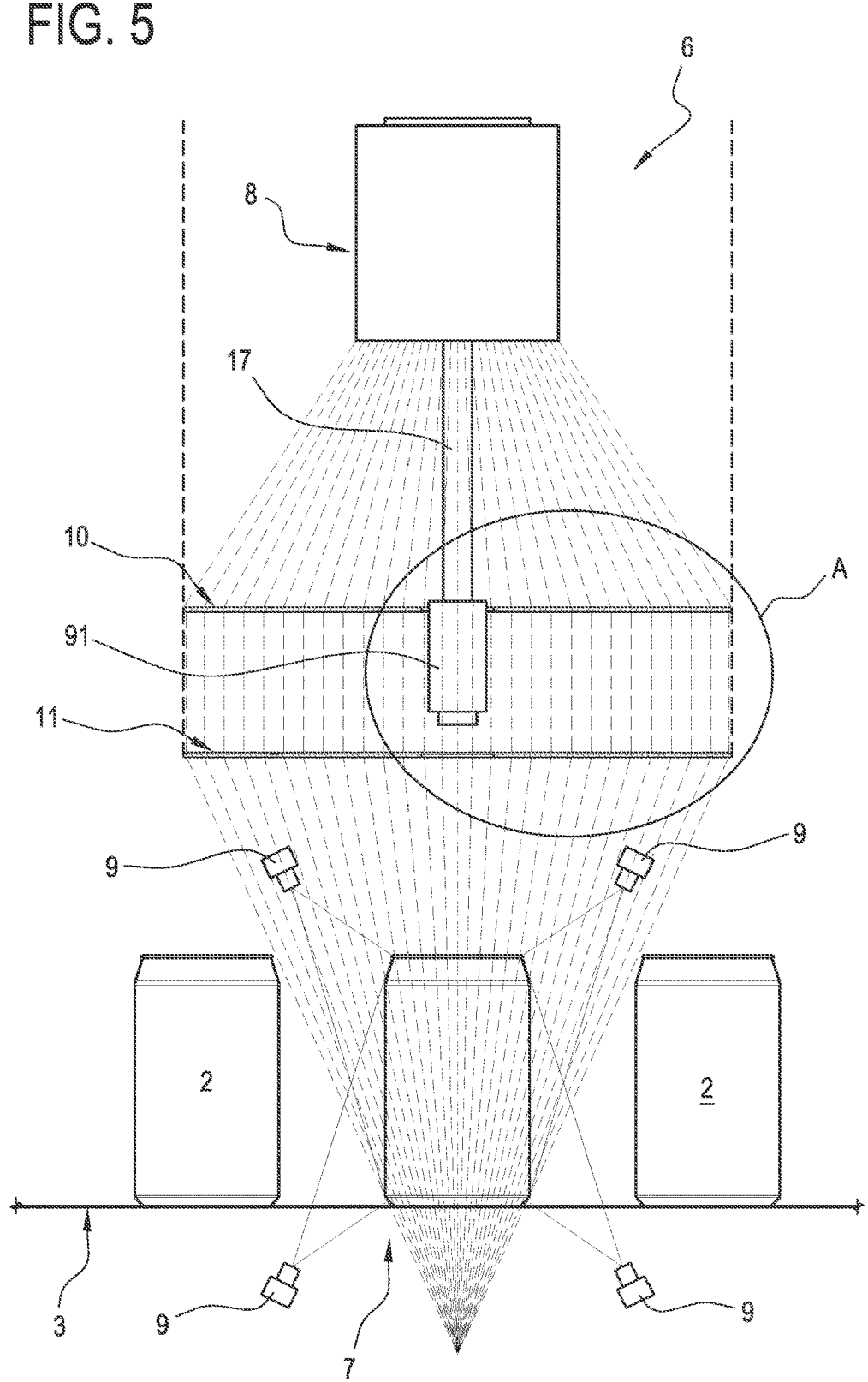
FIG. 5 is a schematic side view of the apparatus of FIG. 2.

The optical inspection apparatus 6 illustrated in FIGS. 2 and 3 comprises an inspection station 7, a lighting system 8 (or illuminator) and one or more cameras 9 directed towards the inspection station 7 to capture an image of the lateral surface of the object 2 to be inspected. In the example illustrated, the apparatus has four cameras 9. Preferably, the apparatus has at least one camera 9 on each of the two opposite sides of the conveyor on which the objects 2 are supported one by one as they reach the inspection station 7. In the example illustrated, the apparatus has two cameras 9 for each of the two sides of the conveyor.

The object 2 to be inspected is positioned in the inspection station 7 oriented along a longitudinal, preferably vertical, axis.

More specifically, the camera 9 is directed towards the inspection station 7 along a viewing axis which is transverse, that is, inclined, to the longitudinal axis of the object 2.

The optical inspection apparatus 6 also comprises collimating means 10 (or a collimating unit or element) associated with the lighting system 8 to direct a beam of collimated light rays towards the object 2 to be inspected, located in the inspection station 7.

More specifically, the collimating means 10 direct a beam of collimated light rays from above towards the object 2 to be inspected, located in the inspection station 7.

The inspection apparatus 6 also comprises a converging lens 11 positioned to face the object 2 to be inspected, which is located in the inspection station 7, and oriented in such a way as to make the collimated light rays from the collimating means 10 converge on the object 2.

More specifically, the converging lens 11 is positioned above the object 2 to be inspected, located in the inspection station 7.

More specifically, the converging lens 11 is a first Fresnel lens.

A possible distance between the first Fresnel lens and the inspection station 7 is such that the latter is positioned in the focus of the first Fresnel lens. This distance is preferably chosen in such a way as to guarantee maximum uniformity of illumination on the lateral surface of the object to be inspected.

More specifically, the collimating means 10 are defined by a second Fresnel lens.

A possible distance between the second Fresnel lens and the lighting system 8 is such that the latter is positioned in the focus of the second Fresnel lens. This distance is preferably chosen in such a way as to guarantee maximum uniformity of illumination on the lateral surface of the object to be inspected.

Alternatively, the collimating means 10 may be defined by a honeycomb grid or two optical filters placed at 90° to each other.

The first and second Fresnel lenses lie in respective parallel planes.

The planes in which the first and second Fresnel lenses lie are parallel to the plane in which the objects are fed through the inspection station 7.

The first and second Fresnel lenses have respective central axes of symmetry 12 which coincide with each other.

The central axes 12 are aligned with the inspection station 7.

The central axes 12 are orthogonal to the plane in which the objects are fed through the inspection station 7.

In an example embodiment, the apparatus also comprises an upper camera 91 configured to view the object 2 to be inspected in the inspection station 7 from above, along an optical path oriented longitudinally.

In an example embodiment, the upper camera 91 is interposed between the collimating means 10 and the converging lens 11.

Preferably, the converging lens 11 (the first Fresnel lens) is centrally perforated; that is to say, it defines a central hole which is coaxial with a longitudinal viewing axis of the upper camera 91.

Preferably, the collimating means 10 (the second Fresnel lens) are centrally perforated; that is to say, they define a central hole which is coaxial with a longitudinal viewing axis of the upper camera 91.

The lighting system 8 comprises at least one ring 14 of LED lights extending around a respective axis of symmetry coaxial with the aforementioned central axes 12.

In an example embodiment, the apparatus comprises a cylindrical tubular element 15 configured to convey the light rays towards the second Fresnel lens. In one example, the tubular element 15 is positioned between the lighting system 8 and the second Fresnel lens. For example, the tubular element 15 is positioned around the lighting system 8 (that is, around the ring of LED lights 14) to surround it.

The element 15 supports the camera 9 by means of a tubular rod 17 which passes through a central hole 18 of the second Fresnel lens.

In one example, the rod 17 also acts as a cable duct for the upper camera 91.

The apparatus according to one or more of the aspects of the present description offers, among others, one or more of the following advantages:
- only the object to be inspected is illuminated while the objects adjacent to it remain unlit;
- the size and weight of the inspection apparatus are limited;
- the camera 91 does not create an unwanted shadow on the inspection station,
- the illumination on the lateral surface of the object 2 to be illuminated is uniform and well balanced.

The present description also provides a method for optical inspection of objects.

This method comprises a step of transporting a plurality of objects (to be inspected) in succession, along a feed path.

The method comprises a step of positioning objects in an inspection station arranged along the feed path.

In the inspection station, at least one of the objects is oriented along a longitudinal axis and defines a support surface and a side surface.

Said positioning, in one embodiment, is done without stopping (or slowing down) the transport of the objects along the feed path.

In one embodiment, the objects are placed in the inspection station one at a time, in succession.

The method comprises a phase of illuminating the object positioned in the inspection station. Such illuminating is a substantially overhead lighting. In one embodiment, the illuminating is realized by a lighting system placed above the inspection station.

The method comprises a step of acquiring (at least) an image of the side surface of the object positioned in the inspection station (and illuminated); i.e., the image includes at least image data representative of the object side surface.

In one embodiment, this acquisition takes place via at least one camera; said camera, in one embodiment, is oriented towards the inspection station; said camera, in one embodiment, is oriented according to the longitudinal axis defined by the lighting system; the object to be inspected, at the instant of acquisition, is located in the inspection station, aligned with its axis with respect to said longitudinal axis. In this regard, it is noted that the object is elongate along an axis, and/or it defines its own axis (for example symmetry axis).

The method also comprises a step of orienting rays generated (by the lighting system), for longitudinally directing a beam of collimated light rays towards the object to be inspected, placed in the inspection station.

Thus, the lighting step includes generating a beam of rays, which are then collimated (through orientation, that is, deviation of the same or at least a part of them).

The method also comprises a step of (further) orientating of the rays of said beam of collimated light rays, to make them converge towards the side surface of the object to be inspected.

In one embodiment, said (additional) orientating takes place via a convergent lens, operatively interposed between the collimating means and the object to be inspected.

In one embodiment, the illuminating of the object comprises a step of generating light beams through a substantially point source; these rays are then collimated parallel to the longitudinal axis and subsequently oriented in a convergent way.

The invention claimed is:

1. An apparatus for optical inspection of objects transported in succession on a conveyor line, comprising:
   an inspection station where at least one of the objects is to be oriented along a longitudinal axis and define a resting surface and a lateral surface, wherein the lateral surface of the object is to extend at least partially about the longitudinal axis when the object is oriented along the longitudinal axis in the inspection station;
   a conveyor for transporting the objects in succession on the conveyor line;
   a lighting system positioned above the inspection station;
   at least one camera located at a side of the conveyor and directed towards the inspection station to capture an image of the lateral surface of the object to be inspected;
   a collimating lens associated with the lighting system to direct a beam of collimated light rays longitudinally towards the object to be inspected, while the object is located in the inspection station; and
   a converging lens that is positioned to face the object to be inspected, and oriented in such a way as to make the collimated light rays converge on the object, while the object is located in the inspection station, wherein the collimating lens and the converging lens are aligned along the longitudinal axis that the object is to be oriented along during inspection of the object within the inspection station.

2. The apparatus according to claim 1, wherein the converging lens is a first Fresnel lens.

3. The apparatus according to claim 1, further comprising a Fresnel lens.

4. The apparatus according to claim 3, wherein the collimating lens and the Fresnel lens lie in respective parallel planes.

5. The apparatus according to claim 4, wherein the collimating lens is a second Fresnel lens, wherein the second Fresnel lens and the Fresnel lens have respective central axes of symmetry which coincide with each other.

6. The apparatus according to claim 1 further comprising an upper camera configured to view the object to be inspected in the inspection station from above, along an optical path oriented longitudinally.

7. The apparatus according to claim 6, wherein the upper camera is interposed between the collimating lens and the converging lens.

8. The apparatus according to claim 6, wherein the converging lens is a first Fresnel lens and the collimating lens comprises a second Fresnel lens, wherein the first and the second Fresnel lenses each define a central hole which is coaxial with a longitudinal viewing axis of the upper camera.

9. The apparatus according to claim 1 further comprising a cylindrical tubular element which is black inside and which surrounds the lighting system to convey the light rays towards the collimating lens.

10. The apparatus according to claim 1, wherein the lighting system comprises at least one ring of LED lights extending around a respective axis of symmetry coaxial with a central axis of symmetry common to the converging lens and the collimating lens.

11. A line for production of objects comprising:
a conveyor line for transporting the objects;
an enamel applicator, located along the conveyor line, for applying an enamel to an outside surface of the objects;
an oven for drying the enamel applied to the objects, and located along the conveyor line, downstream of the enamel applicator; and
an optical inspection apparatus according to claim 1, positioned along the conveyor line, downstream of the oven.

12. A method of optically inspecting objects, the method comprising:
transporting a plurality of objects in succession with a conveyor, along a feed path;
positioning the objects in an inspection station arranged along the feed path, wherein, in the inspection station, at least one of the objects is oriented along a longitudinal axis and defines a support surface and a side surface;
illuminating the object positioned in the inspection station, via a light source positioned above the inspection station;
with at least one camera located at a side of the conveyor and oriented towards the inspection station, acquiring an image of the side surface of the illuminated object positioned in the inspection station;
orientating rays generated by the light source with a collimating lens, for longitudinally directing a beam of collimated light rays toward the object to be inspected, placed in the inspection station; and
orientating rays of said beam of collimated light rays, through a converging lens, for generating a beam of converging rays to illuminate the side surface of the object positioned in the inspection station, wherein
the collimating lens and the converging lens are aligned along the longitudinal axis that the object is to be oriented along during inspection of the object within the inspection station.

13. The method according to claim 12, wherein illuminating the object comprises generating light rays through operation of the light source as a point source, wherein said rays are then collimated parallel to the longitudinal axis and subsequently oriented in a convergent way.

14. An apparatus for optical inspection of objects transported in succession on a conveyor line, comprising:
an inspection station where at least one of the objects is to be oriented along a longitudinal axis, the object, when oriented along the longitudinal axis at the inspection station, comprising: (i) a resting surface, and (ii) a lateral surface accessible for optical inspection;
a conveyor for transporting the objects in succession on the conveyor line;
a lighting system positioned above the inspection station;
at least one camera directed towards the inspection station to capture an image of the lateral surface of the object to be inspected;
a collimating lens associated with the lighting system to direct a beam of collimated light rays longitudinally towards the object to be inspected, while the object is located in the inspection station; and
a converging lens that is positioned to face the object to be inspected, and oriented in such a way as to make the collimated light rays converge on the object, while the object is located in the inspection station,
wherein the least one camera includes a first camera, located at a first side of the conveyor, and a second camera, located at a second side of the conveyor, opposite the first side, for viewing the lateral surface of the object located in the inspection station from opposite sides.

15. The apparatus according to claim 1, wherein the least one camera includes a first camera, located at a first side of the conveyor, and a second camera, located at a second side of the conveyor, opposite the first side, for viewing the lateral surface of the object located in the inspection station from opposite sides.

16. The apparatus according to claim 3, comprising a cylindrical tubular element configured to convey the light rays towards the Fresnel lens.

17. The apparatus according to claim 6, wherein the upper camera is supported through a rod which passes through a hole provided in the collimating lens.

18. The apparatus according to claim 17, wherein the rod provides a cable duct for the upper camera.

19. The apparatus according to claim 1, wherein the lighting system includes one single light source, aligned with the longitudinal axis of the object.

20. The method according to claim 12, wherein the least one camera includes a first camera, located at a first side of the conveyor, and a second camera, located at a second side of the conveyor, opposite the first side, for acquiring images of opposite sides of the lateral surface of the object located in the inspection station.

* * * * *